United States Patent
Park et al.

(10) Patent No.: US 11,111,528 B2
(45) Date of Patent: Sep. 7, 2021

(54) METHOD AND APPARATUS FOR ULTRASENSITIVE QUANTIFICATION OF MICRORNA USING AN ATOMIC FORCE MICROSCOPE AND A HYBRID BINDING DOMAIN

(71) Applicants: POSCO, Pohang-si (KR); POSTECH ACADEMY-INDUSTRY FOUNDATION, Pohang-si (KR)

(72) Inventors: Joon Won Park, Seoul (KR); Joung Hun Kim, Seoul (KR); Young Kyu Kim, Yeosu-si (KR); Hyun Seo Koo, Seoul (KR); Yoon Hee Lee, Seoul (KR)

(73) Assignees: POSCO, Pohang-si (KR); POSTECH ACADEMY-INDUSTRY FOUNDATION, Pohang-si (KR)

(*) Notice: Subject to any disclaimer, the term of this patent is extended or adjusted under 35 U.S.C. 154(b) by 636 days.

(21) Appl. No.: 15/412,025

(22) Filed: Jan. 22, 2017

(65) Prior Publication Data

US 2017/0233799 A1    Aug. 17, 2017

(30) Foreign Application Priority Data

Nov. 23, 2015 (KR) ........................ 10-2015-0164100

(51) Int. Cl.
*C12Q 1/6837* (2018.01)
*G01Q 60/42* (2010.01)
*G01Q 60/38* (2010.01)

(52) U.S. Cl.
CPC ........... *C12Q 1/6837* (2013.01); *G01Q 60/38* (2013.01); *G01Q 60/42* (2013.01)

(58) Field of Classification Search
None
See application file for complete search history.

(56) References Cited

U.S. PATENT DOCUMENTS 8,067,169 B2    11/2011    Sahin et al.
2003/0224370 A1*   12/2003    Rassman ............. C12Q 1/6837
506/9

OTHER PUBLICATIONS

David P. Bartel, "MicroRNAs: Target Recognition and Regulatory Functions", Journal, Leading Edge Review, Cell 136, pp. 215-233, Jan. 23, 2009. Elsevier Inc.
Peter Hinterdorfer and Yves F Dufrêne, "Detection and localization of single molecular recognition events using atomic force microscopy", Nature Methods, vol. 3, No. 5, pp. 347-355, May 2006.
Pieter Mestdagh et al., "Evaluation of quantitative miRNA expression platforms in the micro RNA quality control (miRQC) study", Nature Methods, vol. 11, pp. 809-815, 2014.
Sudhir Husale; Henrik H. J. Persson; and Ozgur Sahin, "DNA nanomechanics allows direct digital detection of complementary DNA and microRNA targets", Nature, vol. 462, pp. 1075-1078, 2009, Macmillan Publishers Limited.

* cited by examiner

*Primary Examiner* — G Steven Vanni
(74) *Attorney, Agent, or Firm* — Don D. Cha; HDC Intellectual Property Law, LLP

(57) ABSTRACT

The present invention provides an apparatus and a method for detecting the presence of and/or determining the amount of a label-free microRNA using an atomic force microscope. The method is extremely selective and/or ultrasensitive. In particular, the present invention provides a cantilever comprising a probe that selectively binds to a double strand of DNA/RNA hybrid complex. The probe comprises a hybrid binding domain (HBD) or a variant thereof.

17 Claims, 6 Drawing Sheets

Specification includes a Sequence Listing.

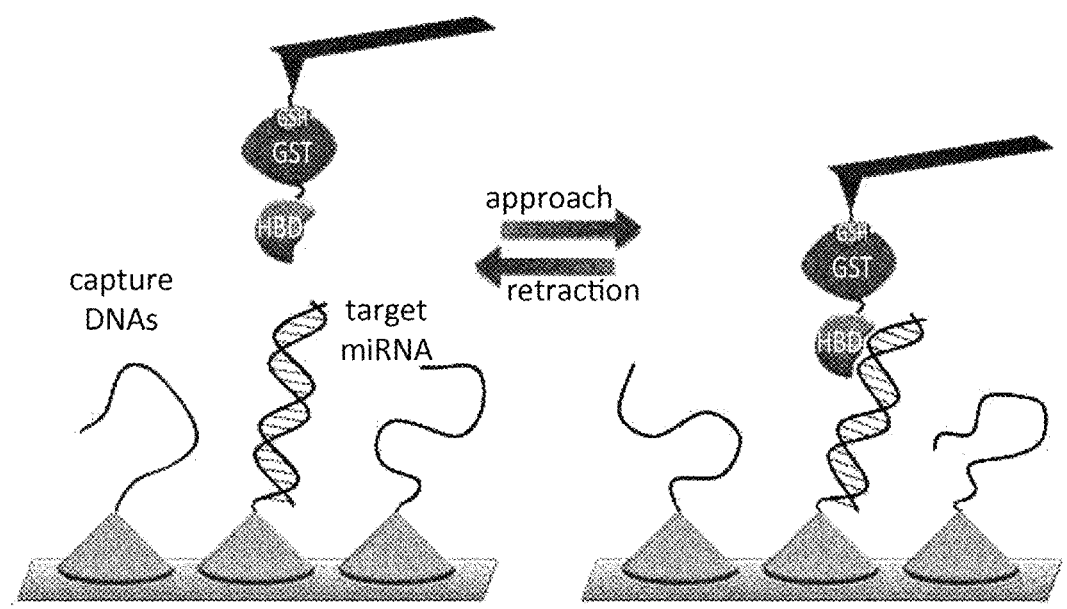
FIG. 2
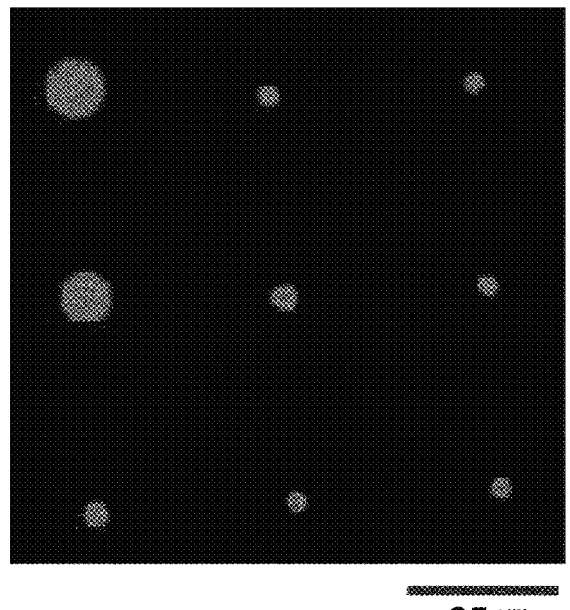
FIG. 3  25μm

METHOD AND APPARATUS FOR ULTRASENSITIVE QUANTIFICATION OF MICRORNA USING AN ATOMIC FORCE MICROSCOPE AND A HYBRID BINDING DOMAIN

CROSS-REFERENCE TO RELATED APPLICATIONS

This application claims the priority benefit of Korean Patent Application No. 10-2015-0164100, filed on Nov. 23, 2015, which is incorporated herein by reference in its entirety.

FIELD OF THE INVENTION

The present disclosure relates to an apparatus for ultrasensitive quantification of a microRNA (miRNA) and a method for using the same. In particular, the present invention relates to detecting a label-free miRNA by adhesion force-mapping using an atomic force microscope (AFM).

BACKGROUND OF THE INVENTION

A microRNA (miRNA) is a noncoding single-stranded RNA typically consisting of 19 to 25 base sequences. It was first discovered in *Caenorhabditis elegans* in 1993. Subsequently, miRNA has been discovered in other species including humans. Recently, miRNA has received a considerable attention because of the sequence homology between species. See, for example, D. P. Bartel, *Cell*, 2009, 136, 215-233. It has been shown a miRNA binds to a specific messenger RNA to cleave the specific messenger RNA or suppress its translation, thereby regulating a protein production. The miRNA is known to be involved in 30% or more of the whole gene expression of the human and serves to finely adjust various biological functions such as cell proliferation, death, development and differentiation.

Studies on abnormal expression of the miRNA and association with various diseases have been actively conducted and particularly, the association with cancer has been mainly reported. Accordingly, studies to utilize miRNAs in living tissues, cells and body fluids in early diagnosis, prognosis, and development of treatment methods of diseases have continued, and a high-sensitive miRNA analysis method, capable of analyzing single cells has been required to distinguish tumor cells at the early stage.

Currently, quantification of the miRNA has been conducted by using a microarray and a reverse transcription-polymerase chain reaction (RT-PCR) which have been used in DNA and RNA analysis. However, it is not straightforward to use these techniques for the miRNA analysis due to short lengths of miRNAs (22 nucleotides in average). In the case of the microarray, the short length of miRNA limits the selection of the probe DNA sequence, and thus the standardization of melting temperature, which is necessary for simultaneous analysis of various miRNAs is limited. The sensitivity of microarray method is 1 pM due to a background noise signal. In the case of conventional RT-PCR, lengths of the primer DNA are similar to the length of miRNA and they cannot be used to amplify miRNAs. The above problems are partially solved by introducing techniques such as locked nucleic acid (LNA), DNA having a hairpin structure, and extension of miRNA using polyadenylation or nucleic acid ligation, but these techniques accompany the increases in analysis time, costs, and the error rate and it has been reported that there is discrepancy in results from different platforms (manufacturers) (P. Mestdagh, et al. *Nat. Methods,* 2014, 11, 809-815.

Accordingly, a miRNA quantification method has not yet achieved reproducibility and reliability to analyze the small numbers of miRNA, such as miRNAs in a single cell (the average number of miRNAs in the single cell has been estimated at 500).

Atomic force microscope can perform a 3D surface imaging with spatial resolution at a nanometer level and detect interaction force between a tip and the sample surface at a few picoNewton (pN) level. Since the analysis can be performed under a physiological condition, various information on wide variety of biomolecules (e.g., structures, dynamics, and distributions) can be determined or analyzed by measuring interaction force between single biomolecules (e.g., DNA-DNA, DNA-RNA, antigen-antibody, protein-ligand, etc.). See, for example, P. Hinterdorfer, et al. *Nat. Methods,* 2006, 3, 347-355.

U.S. Pat. No. 8,067,169 ("the '169 Patent") describes a method for detecting a short nucleic acid on a flat solid surface using an atomic force microscope and a T-shaped cantilever. In this method, a single-stranded probe DNA is immobilized on solid surface, and the cantilever detects the difference in stiffness between a single-stranded probe DNA and a target hybridized duplex.

While this method can potentially be used to detect miRNAs (see, for example, S. Husale, et al. *Nature,* 2009, 462, 1075-1078), there are numerous shortcomings and limitations. For example, the method disclosed in the method disclosed in the '169 Patent cannot eliminate false-positive signals when unrelated molecules in the sample have the similar stiffness to duplex nucleic acids. In addition, the method disclosed in the '169 Patent is only applicable on a flat and rigid solid surface. Furthermore, in the method disclosed in the '169 Patent a primary miRNA (pri-miRNA) and a precursor miRNA (pre-miRNA) cannot be distinguished from each other.

At least in part because of these limitations and shortcomings, there is a need for a more accurate and/or selective method of detecting miRNA using atomic force microscopy.

SUMMARY OF THE INVENTION

An object to be achieved by the present disclosure is to provide a cantilever for an atomic force microscope. The cantilever of the invention comprises a hybrid binding domain (HBD) or a variant thereof in which a DNA/RNA hybrid binds to a tip of said cantilever. Unless stated otherwise, it should be appreciated that a "tip" of the cantilever refers to the probing tip that is used to measure the atomic force interaction.

Another object to be achieved by the present disclosure is to provide an analysis kit comprising the cantilever disclosed herein.

Yet another object to be achieved by the present disclosure is to provide a method for detecting the presence of miRNA. The method can also be used for quantification of a target miRNA. Quantification of a target miRNA in a given sample can be achieved by inter alia calculating the number of miRNAs in a sample from the number of double helixes formed by a probe DNA spot that is immobilized on a substrate, and detecting the presence of DNA/miRNA hybrid complex formed on the substrate using the cantilever of the invention to provide adhesion force-mapping of the substrate.

As can be seen herein, the present invention provides an ultrasensitive method for detecting a label-free miRNA using an atomic force microscope configured with a cantilever disclosed herein. In one particular embodiment, the cantilever comprises an immobilized probe on its tip (i.e., probing tip). In some embodiments, the probe comprises a hybrid binding domain (HBD). Yet in other embodiments, the HBD is adapted to bind to a DNA-RNA hybrid complex. In other embodiments, the probe is immobilized and a quantification apparatus comprises a reference miRNA.

According to one particular aspect of the present invention, there is provided a cantilever for an atomic force microscope. The cantilever for an atomic force microscope includes: a body; a tip formed at an end of the body; and includes a hybrid binding domain (HBD) or a variant thereof which is immobilized on the surface of the tip and is adapted to bind to a minor groove of a DNA/RNA hybrid complex in a non-sequence specific manner.

According to another aspect of the present disclosure, there is provided a kit for ultrasensitive quantification of a miRNA. The kit includes: a cantilever disclosed herein; a substrate to which a probe DNA that has a target miRNA-complementary base sequence is immobilized; and a reference sample including the target miRNA.

Yet another aspect of the present invention provides a method for quantification of miRNAs. The method for quantification of a miRNA includes: (a) forming a probe DNA spot by immobilizing a probe DNA that has a base sequence complementary to a target miRNA; and (b) forming a DNA/RNA hybrid double helix complex consisting of the probe DNA and the target miRNA by contacting a sample. It should be noted that when the sample comprises the target miRNA, it forms a complex on the probe DNA spot. The method also includes (c) performing an adhesion force-mapping the spot by using the cantilever and determining the presence of DNA/RNA hybrid double helix complex in the spot where the adhesion force is observed; and (d) determining the number of miRNAs in the sample by counting the number of double helixes on the spot.

BRIEF DESCRIPTION OF THE DRAWINGS

FIG. 2 is a schematic diagram illustrating that a HBD immobilized to a cantilever tip is bound to or separated from a probe DNA/miRNA double helix of the substrate surface according to approach and retraction of the cantilever;

FIG. 3 illustrates that probe DNA spots having various sizes are prepared by using a fluorescent molecule-labeled probe DNA and verified by a fluorescent microscope;

DETAILED DESCRIPTION OF THE INVENTION

Figure 1:
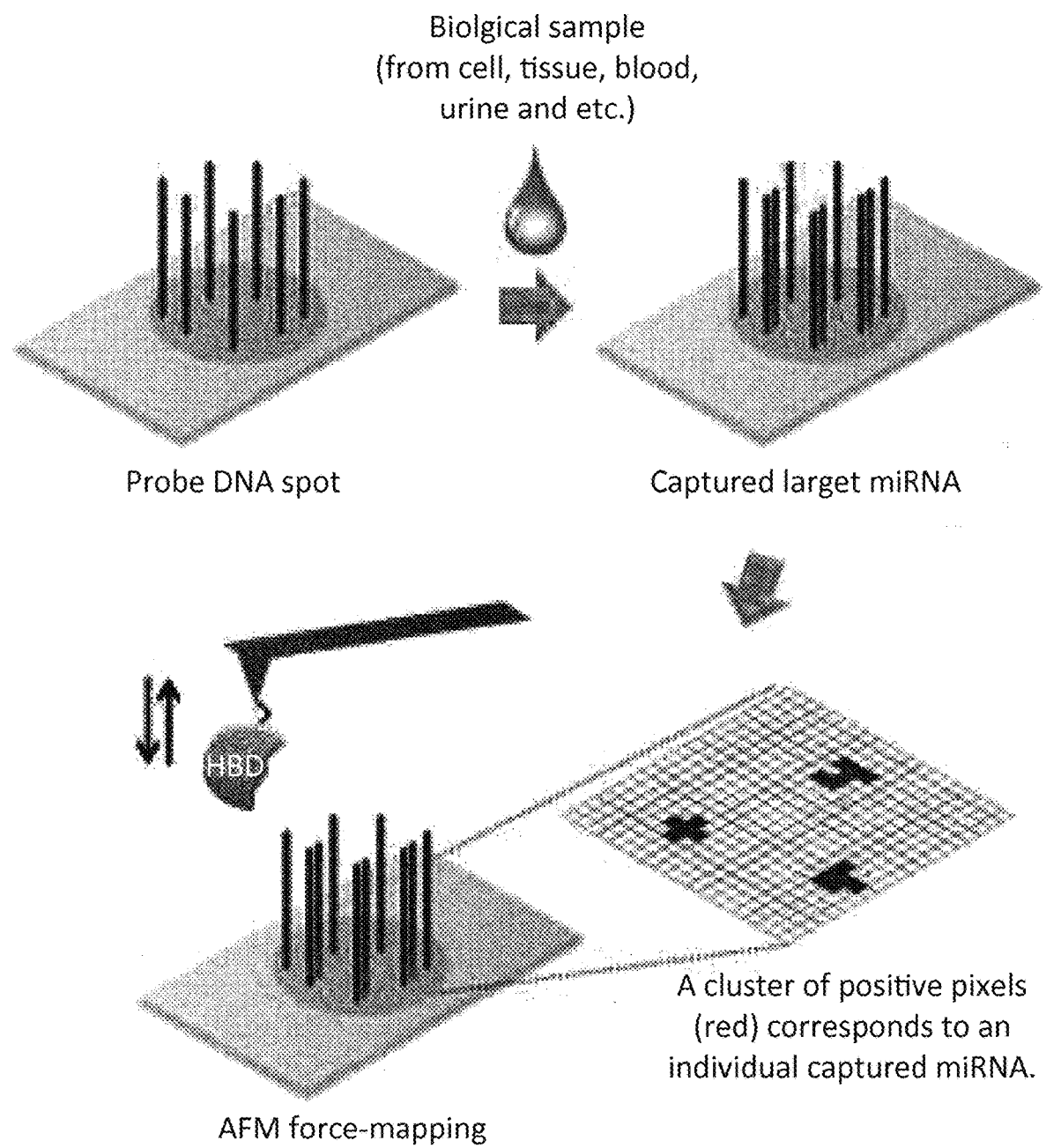
FIG. 1 is a schematic diagram illustrating a target miRNA analysis principle using an AFM according to the present disclosure.

The shapes, sizes, ratios, angles, numbers, and the like illustrated in the accompanying drawings for describing the exemplary embodiments of the present disclosure are merely examples, and the present disclosure is not limited thereto. Like reference numerals generally denote like elements throughout the present specification. Further, in the following description, a detailed explanation of known related technologies may be omitted to avoid unnecessarily obscuring the subject matter of the present disclosure. The terms such as "including," "having," and "consist of" used herein are generally intended to allow other components to be added unless the terms are used with the term "only". Any references to singular may include plural unless expressly stated otherwise.

Components are interpreted to include an ordinary error range even if not expressly stated.

When the position relation between two parts is described using the terms such as "on", "above", "below", and "next", one or more parts may be positioned between the two parts unless the terms are used with the term "immediately" or "directly".

When an element or layer is referred to as being "on" another element or layer, it may be directly on the other element or layer, or intervening elements or layers may be present.

Although the terms "first", "second", and the like are used for describing various components, these components are not confined by these terms. These terms are merely used for distinguishing one component from the other components. Therefore, a first component to be mentioned below may be a second component in a technical concept of the present disclosure.

Throughout the whole specification, the same reference numerals denote the same elements.

Since size and thickness of each component illustrated in the drawings are represented for convenience in explanation, the present disclosure is not necessarily limited to the illustrated size and thickness of each component.

The features of various embodiments of the present disclosure can be partially or entirely bonded to or combined with each other and can be interlocked and operated in technically various ways, and the embodiments can be carried out independently of or in association with each other.

Hereinafter, various exemplary embodiments of the present disclosure will be described. The present disclosure may be implemented in various modifications and various exemplary embodiments, and the following specific exemplary embodiments are merely examples and the present disclosure is not limited thereto. It should be understood that the present disclosure includes all modifications, equivalents, and alternatives included in the spirit and the scope of the present disclosure.

One aspect of the invention provides a cantilever that is useful in an atomic force microscopy. The cantilever of the invention overcomes the various limitations and shortcomings described in the Background of the Invention section above. The cantilever for an atomic force microscope according to an embodiment of the present disclosure includes: a body; and a tip formed at an end of the body, and includes a probe which is immobilized on the surface of the tip and binds to a minor groove of a DNA/RNA hybrid duplex in the non-sequence specific manner. In one particular embodiment, the probe comprises a hybrid binding domain (HBD) or a variant thereof. The probe is capable of binding to a DNA/RNA complex but not to a single strand DNA or a DNA/DNA complex. Thus, the probe of the invention can distinguish between DNA/RNA hybrid complex from that of a single stranded DNA or a DNA/DNA duplex.

In one particular embodiment, the hybrid binding domain is a domain at an amino terminal (N-terminal) of a human ribonuclease 1 (RNase I) and specifically bind to a double helix strand of the DNA/RNA hybrid, and HBD has two separate regions that independently bind to RNA and DNA. Preferably, the HBD consist of an amino acid sequence of SEQ ID NO: 1.

In one embodiment, the HBD variant comprises a fusion protein with glutathione S-transferase (GST). In one particular embodiment, the GST-HBD fusion protein is expressed in which the GST is linked to the N-terminal of the HBD. In this manner, the GST portion of the fusion protein can be immobilized to the cantilever tip. One or more variants, such as GST can be selected for the orientation-controlled immobilization of HBD. In another embodiment, HBD variant is selected from the group consisting of GST linked HBD, histidine-tag linked HBD, biotinylated HBD, and an HBD comprising a site-specific mutation. The immobilization of HBD or a variant thereof with a constant orientation leads to an increased reproducibility of the analysis. In one particular embodiment, the HBD variant is a GST-HBD fusion protein.

Still in another embodiment, the HBD variant is a GST linked HBD. In some instances, the GST moiety is connected to the N-terminal of the HBD. In this instances, the GST moiety is immobilized to cantilever and the carboxy terminal (C-terminal) of the HBD is oriented away from the cantilever tip surface, i.e., toward an opposite direction to the probing tip of the cantilever.

To detect the presence of or to quantify the amount of a target miRNA in a sample, the sample (which may or may not include the target miRNA) is contacted with the substrate on which the probe DNA is immobilized under conditions sufficient to form a probe DNA-target miRNA hybrid complex, when the target miRNA is present in the sample. The probe DNA includes the base (or nucleotide) sequence that is complementary to the target miRNA. In this manner, if the sample contains the target miRNA, a DNA/RNA (i.e., probe DNA-target miRNA) hybrid complex is formed. The presence of or the quantification of the target miRNA can then be determined by an atomic force microscopy ("AFM") using a cantilever disclosed herein.

In one particular embodiment, the hybrid binding domain or the variant thereof is capable of or adapted to binding to a minor groove of the DNA/RNA hybrid complex in the non-sequence specific manner. In some embodiments, the site of the DNA/RNA hybrid complex bound with the hybrid binding domain or the variant thereof is a 2'—OH group of two consecutive bases of the RNA strand and/or three phosphodeoxyribose units of the DNA strand.

Yet in another embodiment, the site of the hybrid binding domain binding to the DNA/RNA hybrid is (i) Y3, K33, and K34 of the HBD bound with the DNA strand of the DNA/RNA hybrid complex, (ii) W17 and F32 of the HBD bound with the RNA strand of the DNA/RNA hybrid, or (iii) a combination thereof.

Still in another embodiment, the target miRNA is derived from a single cell.

Another aspect of the invention provides a kit detecting the presence of or a quantification of miRNA. In some embodiments, the kit can be used for ultrasensitive quantification miRNA. Still in other embodiments, the kit includes a cantilever disclosed herein, and a substrate to which a probe DNA is attached on the surface of the substrate. In one particular embodiment, the probe DNA includes a complementary base sequence to a target miRNA. In other embodiments, the kit also includes a sample and/or the reference target miRNA. Yet in other embodiments, the kit further includes an atomic force microscope.

Yet another aspect of the invention provides a method for detecting the presence or quantifying the amount of a target miRNA in a sample. In some embodiments, the method includes (a) contacting a substrate comprising a probe DNA that is immobilized on the surface of said substrate with a sample under conditions sufficient to form a DNA/RNA hybrid complex when a target microRNA (miRNA) is present in the sample; and (b) detecting a presence of the DNA/RNA hybrid complex using an atomic force microscopy comprising a cantilever disclosed herein. In some embodiments, the probe DNA that is attached to the surface of the substrate comprises a nucleotide sequence that is complementary to the target miRNA. In other embodiments, a probe DNA spot is formed by immobilizing the probe DNA to the surface of the substrate. Still in other embodiments, an adhesion force-mapping of the spot is performed using a cantilever of the invention to determine the presence of DNA/RNA hybrid complex. Typically, the position where the adhesion force is observed is indicative of the presence of the DNA/RNA hybrid complex. The number of miRNAs in the sample can be determined by counting the number of DNA/RNA complexes in the spot.

In some embodiments, the method includes the step of determining the amount of said target miRNA in said sample. Such a method comprises determining the number of the DNA/RNA hybrid complex detected per spot area of the substrate; and calculating the total number of the target miRNA in the sample using Equation 1 below:

$$T_{miRNA}=(N\times(S/U))/(E/100) \qquad (Eq.\ 1)$$

where $T_{miRNA}$=total number of target miRNA in the sample;
N=the number of target miRNA per unit area of spot;
S=total spot area within said substrate;
U=unit area of spot;
E=% capture efficiency of miRNA by said probe.

The capture efficiency (E) is calculated using the synthetic miRNA of the same sequence as the target miRNA. See, for example, *J. Am. Chem. Soc.,* 2016, 138, 11664-11671. Briefly, to quantify a target miRNA in a single cell, a probe DNA spot of 3-8 μm diameter was produced using an AFM-based fluidic tool, and the capture efficiency was evaluated by incubating a synthetic miR-134 solution of 10-100 aM (240-2400 copies in 40 μL) on one such spot. By recording maps at three arbitrary positions within a spot for one sample and taking the average, the number of captured miR-134s on each spot was calculated. From the slope of the linear regression, the capture efficiency of miR-134 on a probe DNA spot was estimated to be 78%.

In one embodiment, the method includes preparing the probe DNA spot and contacting an aqueous solution containing the sample to be analyzed for the presence of or the amount of the target miRNA under conditions sufficient to form probe DNA-target miRNA hybrid complex, when the target miRNA is present in the sample. This can be done by simply placing on the sample on the probe-DNA spot for a time and condition sufficient to allow formation of the hybrid complex. The aqueous solution of the sample can then be washed to remove any non-bound material and creating an adhesion force-mapping using a cantilever of the invention in an aqueous solution. When the probe DNA-target miRNA hybrid complex is present, specific adhesion force between the HBD (present on the cantilever) and the DNA/RNA complex can be observed and the number of miRNA captured in the mapping area can be counted. In addition, by comparing the mapping area and an area of the entire probe DNA spots, the number of miRNAs captured in the entire area can be calculated.

As can be seen, the target miRNA needs not be labeled. Thus, the devices and methods of the invention can be used without the need for labeling the target miRNA. Accordingly, in some embodiments, the target miRNA may not be labeled.

In some embodiments, the sample is a single cell or is derived from a single cell. Still in other embodiments, the target miRNA is derived from a single cell. When a small number of target miRNA is captured on the probe DNA spot having a relatively large area, the number of target miRNA captured per unit area is small, and thus calculation of the number of target miRNA in the entire area from the detected numbers in the scanned partial area is less reliable. Accordingly, for quantification of a small number of target miRNA, such as the total number of target miRNA in a single cell, it is helpful to prepare a probe DNA spot of several microns. That is, depending on the sample (e.g., the amount of target miRNA), probe DNA spots of various sizes (e.g., diameters) are prepared and used to provide a high sensitivity and a wide dynamic range for analysis.

In some embodiments, the method for quantifying the total number of probe DNA-target miRNA complex (and hence the total number of target miRNA in a sample) includes counting the number of probe DNA-target miRNA complex captured per unit area; and calculating the total number of target miRNA in a sample using Equation 1.

For example, it may be determined the double helix (i.e., probe DNA-target miRNA hybrid complex) is present when the adhesion forces are observed at four adjacent pixels of 8 nm pixel size; or at three adjacent pixels of 10 nm pixel size assuming 15 nm as the hydrodynamic radius of the complex of DNA/RNA hybrid and HBD.

The size (diameter) of the probe DNA spot of the present disclosure is determined according to a target miRNA concentration. In some embodiments, the target miRNA concentration ranges from $5 \times 10^{-20}$ to $2 \times 10^{-13}$ M. The diameter of the probe DNA spot can be calculated using equation 2, equation 3, or a combination thereof:

$$S_D = ([M] \times 10^{19}/5)^{0.5} \quad \text{(Equation 2)}$$

$$S_D = ([\text{unit}]/10)^{0.5} \quad \text{(Equation 3)}$$

where $S_D$ is probe DNA spot diameter in μm, [M] is miRNA concentration and [unit] is miRNA number, which is the estimated number of target miRNA in a given sample. The diameter of the probe DNA spot can be chosen to allow the density of the surface-captured target miRNA to be optimal for visualizing each DNA-miRNA duplex. Equation 3 is used for the spot fabrication if the number of target miRNA in the sample can be estimated. And Equation 2 is used if the concentration of target miRNA in the 40 mL solution (total RNA-extracted solution) can be estimated.

As can be seen, using the above Equations, when the target miRNA concentration is in the range from $5 \times 10^{-20}$ to $2 \times 10^{-13}$ M, the size of the probe DNA spot ranges from 1 μm to 200 μm (diameter), respectively.

Typically, the number of DNA/miRNA hybrid complex is determined by performing adhesion force-mapping 1 to 10 times. Generally, adhesion force-mapping is performed from about 2 times to about 5 times, and more often from about 3 times to 5 times. More accurate value can be obtained by averaging the values of the results.

The substrate is not limited to any particular solid material. In general, any material where the probe DNA can be attached is suitable for the methods of the invention. Exemplary substrates that are suitable for the invention include, but are not limited to, glass, metal, plastic, silicon, silicate, ceramic, a semiconductor, synthetic organic metal, a synthetic semiconductor, an alloy, and any combination thereof.

For adhesion force-mapping, the hydrodynamic distance (e.g., the distance between the probe DNA-target miRNA complex on a substrate surface and the probe, such as GST-HBD, on the cantilever, or the distance that allows detection of the presence of the probe DNA-target miRNA hybrid complex using the atomic force microscope disclosed herein) used in methods of the present invention can range from about 20 nm to about 100 nm. The term "hydrodynamic distance" refers to the largest lateral distance (on x-y plane) within which HBD on the tip of a cantilever can find a DNA/miRNA duplex immobilized on surface. For graphic explanation, see Figure S3 of *J. Am. Chem. Soc.* 2016, 138, 11664-11671, which is incorporated herein by reference in its entirety. It should be appreciated that the scope of the invention is not limited to this particular hydrodynamic distance range. In general, any hydrodynamic distance range that can detect the presence of the probe DNA-target miRNA hybrid complex using a cantilever of the invention can be used.

When the pixel size of the force-mapping is smaller than the hydrodynamic distance in which the DNA/miRNA hybrid complex and the probe can bind to each other, the adhesion force is observed in several adjacent pixels with respect to one captured miRNA. For example, in a high-resolution adhesion force-mapping where the hydrodynamic distance is about 30 nm and the pixel size is 8 nm, the adhesion force may needs to be observed in four adjacent pixels in order to ensure that the DNA/miRNA hybrid complex is present at the site. In the case where the pixel size is 10 nm, the adhesion force may needs to be observed in three adjacent pixels to ensure the presence of the DNA/miRNA hybrid complex. In some cases, individual miRNAs can be detected with high reliability by observing a cluster of pixels in which the adhesion force is observed in the high-resolution force-mapping (see, for example, FIGS. 6, 7 and 8).

In adhesion force-mapping, the number of nucleotides of unhybridized portion (that remains as single-stranded) of the DNA/miRNA hybrid complex may range from 0 to about 10 nucleotides, often from 0 to about 6.

The term 'precursor miRNA' used in present specification is premature form of miRNA that has translocated from the nucleus to the cytoplasm and referred to as miRNA having a longer length (for example, 60 to 90 nucleotides) and a hairpin structure which has not been cleaved. While the precursor miRNA can hybridize with the probe DNA, the non-hybridized single-stranded part hinders binding of HBD to DNA/RNA hybrid complex. Therefore, the precursor miRNA is not recognized or detected by atomic force microscopy when a cantilever of the invention is used.

When the DNA in the sample is hybridized with the probe DNA, it is also not recognized or detected by the atomic force microscopy having a cantilever disclosed herein. This non-recognition is due to the fact that HBD of the present disclosure specifically binds to the RNA-DNA double helix complex, and not the DNA-DNA duplex. Accordingly, the apparatus and the methods of the invention significantly reduce or eliminate a false positive signal from any binding of the precursor miRNA to the probe DNA or binding of a DNA to a probe DNA.

As stated herein, the present invention provides a method for detecting the presence of or quantification of a target miRNA in a sample using atomic force microscopy without the need for labeling or amplifying the sample.

In some embodiments, the apparatus and methods of the invention allow an absolute quantification of individual miRNAs without a need for normalization. The sample can be analyzed on a substrate having various elasticity or stiffness. The apparatus and the methods of the invention significantly reduce (e.g., by more than 50%, typically by more than 80% and often by more than 90%, compared to, for example, the method disclosed in the '169 Patent) or eliminate completely any false positive signal that can be generated from binding of the probe DNA to the precursor miRNA or the DNA that may be present in the sample.

Due to a high selectivity and accuracy, the apparatus and methods of the invention allow determination of the presence of or quantification of the target miRNA in a single-cell. Such analysis of single cell allows one skilled in the art to study cell heterogeneity and allows for a single cell diagnostics.

EXAMPLES

Advantages and features of the present disclosure, and methods for accomplishing the same will be more clearly understood from exemplary embodiments described below with reference to the accompanying drawings. However, the present disclosure is not limited to the following exemplary embodiments but may be implemented in various different forms. The exemplary embodiments are provided merely as guidance to one skilled in the art, to which the present disclosure pertains, to practice the present invention.

Example 1: Preparation of Cantilever Tip Immobilized with GST-HBD

In order to immobilize an HBD (SEQ ID NO: 1) to an AFM cantilever tip in an orientation-controlled manner, a fusion protein in which GST connected to an N-terminal of the HBD was produced. To this end, a GST-HBD gene was cloned in pGEX-4T-1. *Escherichia coli* BL21 (DE3) cells were transformed by a gene vector encoding the fusion protein and incubated in an LB culture medium. The expression of the protein was facilitated with 0.2 mM isopropyl-β-D-1-thiogalactopyranoside (IPTG) at 37° C. The cells were lyzed by an ultrasonic wave in a solution containing 0.5% Tween 20 (v/v) and centrifuged (4° C. at 25,000 g) for 25 minutes to separate a supernatant. The GST-HBD was purified using a column filled with GSH-agarose beads. The purified proteins were concentrated and stored at −80° C. before use.

ForceRobot (atomic force microscope) of JPK Instruments Corporation was used. The cantilever (Probe Type B of Nanolnk Corporation) had an average spring constant of about 4 pN/nm in DPN.

For immobilizing the GST-HBD, the cantilever tip was washed and a self-assembled monolayer was formed and a primary amine group was introduced on the surface through modification. Glutathione (GSH) was covalently immobilized to the primary amine group of the cantilever tip using a linker molecule (N-(4-maleimidobutyric acid)hydroxysuccinimide ester (GMBS)). The cantilever tip was immersed in an aqueous solution containing the GST-HBD to immobilize the GST-HBD to the GSH. The cantilever tip was then washed to remove excess GST-HBD before use. A schematic diagram of the completed cantilever tip is illustrated in FIG. 2.

Example 2: 10.0 fM miR-134 Analysis

As schematic illustrated in FIG. 1, a probe DNA spot was prepared by immobilizing the probe DNA to a specific region of the solid surface. Briefly, a glass slide was primed by introducing a primary amine functional group on its surface. The glass slide was washed and a linker molecule (N,N'-disuccinimidyl carbonate (DSC)) was added to the glass slide to allow reaction with the primary amine that is present on the surface.

A probe DNA having the nucleotide sequence 5'-CCC CTC TGG TCA ACC AGT CAC A-3' (SEQ ID NO:3) in which an amine group was attached to a 5' or 3' terminal was used. A small amount of solution (150 mM sodium chloride, 15 mM sodium citrate, 0.17 mM sodium dodecyl sulfate, 14.9 mM betaine, 6.2 mM sodium azide, pH 8.5) containing the probe DNA was placed onto the substrate surface using a microarrayer to prepare the probe DNA spot having an average diameter of 150 micrometers. In order to analyze thousands or less target miRNAs or miRNAs in a single cell, the probe DNA spot having a diameter of several microns was prepared, and in this case, FluidFM of Nanosurf Corporation was used. A solution filled in a cantilever was transferred to the substrate surface through a hole of about 300 nanometers at the end of the cantilever tip. The probe DNA spot having a diameter of 1 to 10 micrometers can be prepared on the substrate surface using the solution. An example of the spot prepared is illustrated in FIG. 3. As shown in FIG. 3, probe DNA spots having various sizes were prepared using fluorescent molecule-labeled probe DNA and verified by a fluorescent microscope.

Target miRNA Hybridization and Binding Force-Mapping:

100 μL of a 10.0 fM miR-134 solution as a target miRNA was placed on the probe DNA spot of the substrate at 34° C. for 20 hrs and then the substrate was immersed in a washing solution and washed while stirring the solution at 45° C. for 15 minutes. The substrate was examined with AFM for the presence of captured miRNAs on the substrate surface in phosphate buffered saline (PBS).

For the adhesion force-mapping, the cantilever tip was moved to the next pixel after repeatedly approaching, contacting, and retracting at a pixel in an area of 240 nm×240 nm with a pixel size of 8 nm (5 times per pixel, and approach and retraction speeds of 1.0 μm/s) (FIG. 2).

Figure 4:
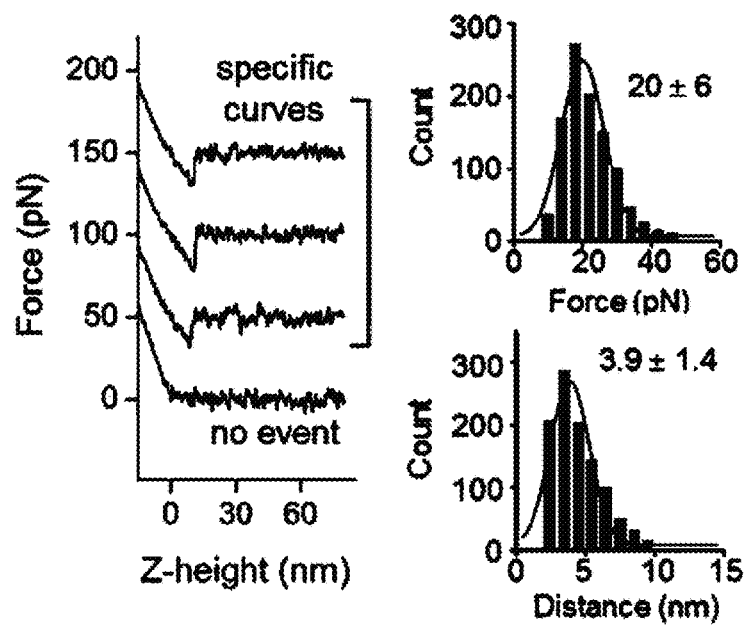
FIG. 4 illustrates a force-distance curve according to a specific binding between the HBD and a double helix of probe DNA/miRNA hybrid and a histogram of adhesion force and a unbinding distance.

When the probe DNA-target miRNA was present on the substrate, a force-distance curve representing specific adhesion between HBD and the DNA/RNA complex was observed. In addition, the adhesion force and unbinding distance values between HBD and the DNA/RNA complex was determined by analyzing the force-distance curve. FIG. 4 is a force-distance curve showing a specific adhesion between HBD and a probe DNA-target miRNA hybrid complex. FIG. 4 also shows a histogram of the adhesion force and unbinding distance.

The force-distance curve and the histogram of the adhesion force and the unbinding distance illustrated in FIG. 4 were values obtained by targeting miRNA 134 (miR-134), and representative values (±standard deviation of distribution) of the adhesion force and the unbinding distance were 20 pN and 3.9 nanometers, respectively, by fitting the histogram of FIG. 4 to a Gaussian distribution. When targeting miR-124 and -486, the adhesion forces were 23 and 19 pN, respectively, and the unbinding distances for both were 3.7 nanometers.

Example 3. 50 aM miR-134 Analysis

To analyze a sample having about 1,200 miRs-134, a probe DNA spot having a diameter of 6.4 μm was prepared by using FluidFM (Nanosurf Corporation). A cantilever having a hole with a diameter of 300 nm was used for adhesion force-mapping. The method for producing the substrate with immobilized probe DNA was performed substantially in the same manner as described in Example 2-1 above.

Figure 7:
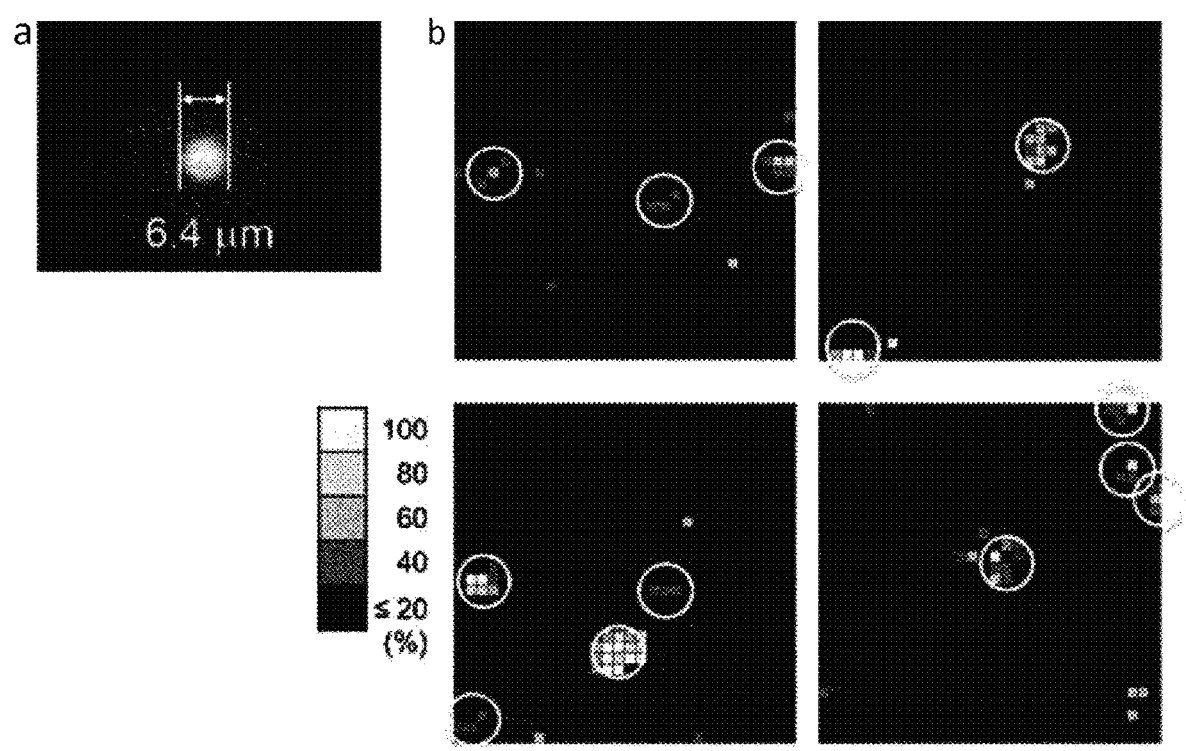
FIG. 7 is an example in which a sample including about 1,200 target miRNAs is analyzed on a probe DNA spot having a diameter of 6.4 μm. Panel A is a fluorescent microscope image of the probe DNA spot and Panel B is a force-map obtained at an arbitrary site in the spot (measured by 300 nm×300 nm, a pixel size of 10 nm, and 5 times per pixel)

Target miRNA Hybridization and Detection by Adhesion Force-Mapping:

A solution of miR-134 (40 μL, 50 aM) was placed on the probe DNA spot. The adhesion force mapping was performed at four sites on the probe DNA spot (300 nm×300 nm, a pixel size of 10 nm, 5 times per pixel, and approach and retraction speeds of 1 μm/s). The sample had about 1,200 target miRNAs. The sample was analyzed using AFM on a probe DNA spot having a size (i.e., diameter) of 6.4 μm. The adhesion force-map (300 nm×300 nm, a pixel size of 10 nm, and 5 times per pixel) was obtained and analyzed at arbitrary sites in the spot. FIG. 7 shows the adhesion force-mapping results on a sample having about 1,200 target miRNAs.

FIG. 7A is a fluorescent microscope image of the probe DNA spot and FIG. 7B is an adhesion force-map obtained at an arbitrary site in the spot (300 nm×300 nm, a pixel size of 10 nm, and 5 times per pixel).

As can be seen, 3, 2, 4, and 4 miR-134 were detected in four regions with an average value thereof of 3.3. Theoretically, hybridization of miR-134 on the probe DNA spot having a diameter of 6.4 μm is expected to produce in an area of 300 nm×300 nm, about 3.4 probe DNA-target miRNA hybrid complex. This coincided well (within ±0.1) with an actual value of 3.3. In order to analyze a small amount of target miRNA, the accuracy of results can be increased by performing the adhesion force-mapping in various regions, and taking the average number.

Example 4: Hybridization with Precursor miRNA and Adhesion Force-Mapping

A cantilever (DPN Probe Type B of NanoInk Corporation) having an average spring constant of about 4 pN/nm was used in a ForceRobot AFM instrument (JPK Instruments Corporation). A probe DNA spot having a diameter of about 150 micrometers was prepared.

Figure 6:
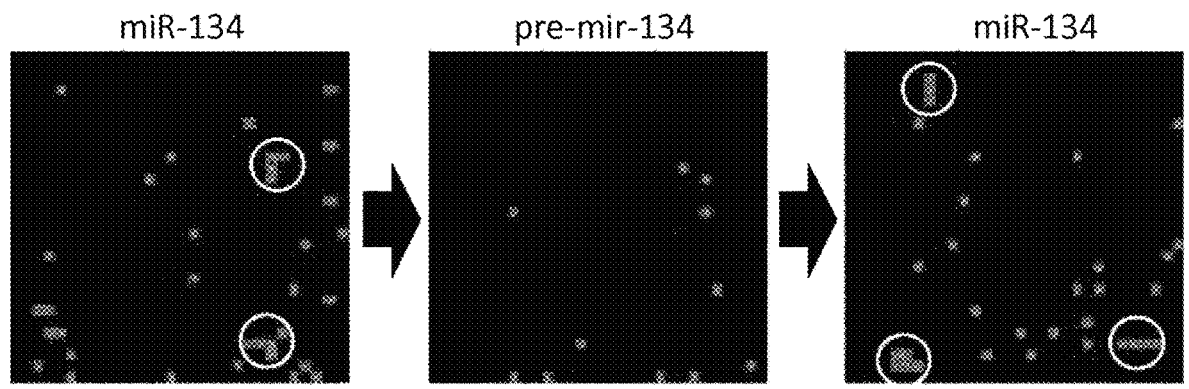
FIG. 6 illustrates observing a cluster (yellow circle) of pixels having adhesion force corresponding to the hybridized miRNA by performing force-mapping with a pixel size of 8 nm. An area where the precursor miRNA is hybridized is also mapped by the same cantilever tip, but the cluster is not observed.

Precursor miRNA Hybridization and Analysis Using Adhesion Force-Mapping:

A 100 μl of 10.0 fM miR-134 solution was hybridized on a probe DNA spot having a diameter of about 150 micrometers in an area of 240 nm×240 nm. The substrate was mapped at an arbitrary site on the probe DNA spot (a pixel size of 8 nm, 5 times per pixel, and approach and retraction speeds of 1.0 μm/s), two miRNAs in the area (a cluster of collecting four or more pixels where the specific adhesion force was observed) was observed (see FIG. 6). FIG. 6 shows a cluster (circle) of pixels having adhesion force corresponding to the presence of the probe DNA-target miRNA hybrid complex. While an area where the precursor miRNA is hybridized to the probe DNA was also detected by the same cantilever, no cluster is observed. This shows one can readily distinguish the probe DNA-target miRNA hybrid complex from the probe DNA-precursor target miRNA hybrid complex.

When the adhesion force-mapping was performed in an area where precursor miRNAs (pre-mir-134) were hybridized at 10.0 fM, the cluster was not observed. In contrast, when the adhesion force-mapping was performed in an area where the miR-134s present (and hence a probe DNA-target miRNA hybrid complex is present), again three clusters were observed. This illustrates that under the adhesion force-mapping conditions, the HBD strongly binds to a mature miRNA/DNA hybrid, but only weakly (below the noise level), if at all, to the precursor miRNA/DNA hybrid. It should also be noted that even when the concentration of pre-mir-134 was increased by 1,000 times, the cluster was not observed. These results indicate even when the probe DNA-precursor miRNA hybrid complex had formed, the HBD did not bind to the duplex in a significant manner.

Example 5: Hybridization with DNA and Adhesion Force-Mapping

In order to verify that the observed adhesion force was due to binding to the probe DNA-target miRNA hybrid complex, adhesion force-mapping was performed (i) before hybridizing the miRNA and (2) after hybridizing the probe DNA with a complementary DNA rather than the target miRNA. The target miRNA was a miR-134 (SEQ ID NO: 2) and the DNA used for testing was a miR-134 homologous DNA having the same sequence (except uracil (U) was replaced with thymine (T)) as miR-134. Both miR-134 and its homologous DNA were present in a 100 μL solution at a concentration of 10.0 μM. This solution was placed on the probe DNA spot, which had a diameter of 150 μm, under conditions sufficient to form the probe DNA-(miR-134) hybrid complex and the probe DNA-(miR-134 homologous DNA) hybrid complex. The adhesion force mapping was conducted on 10.0 μm×10.0 μm area with a pixel size of 500 nanometers (5 times per pixel), and the results are shown in FIG. 5.

Figure 5:
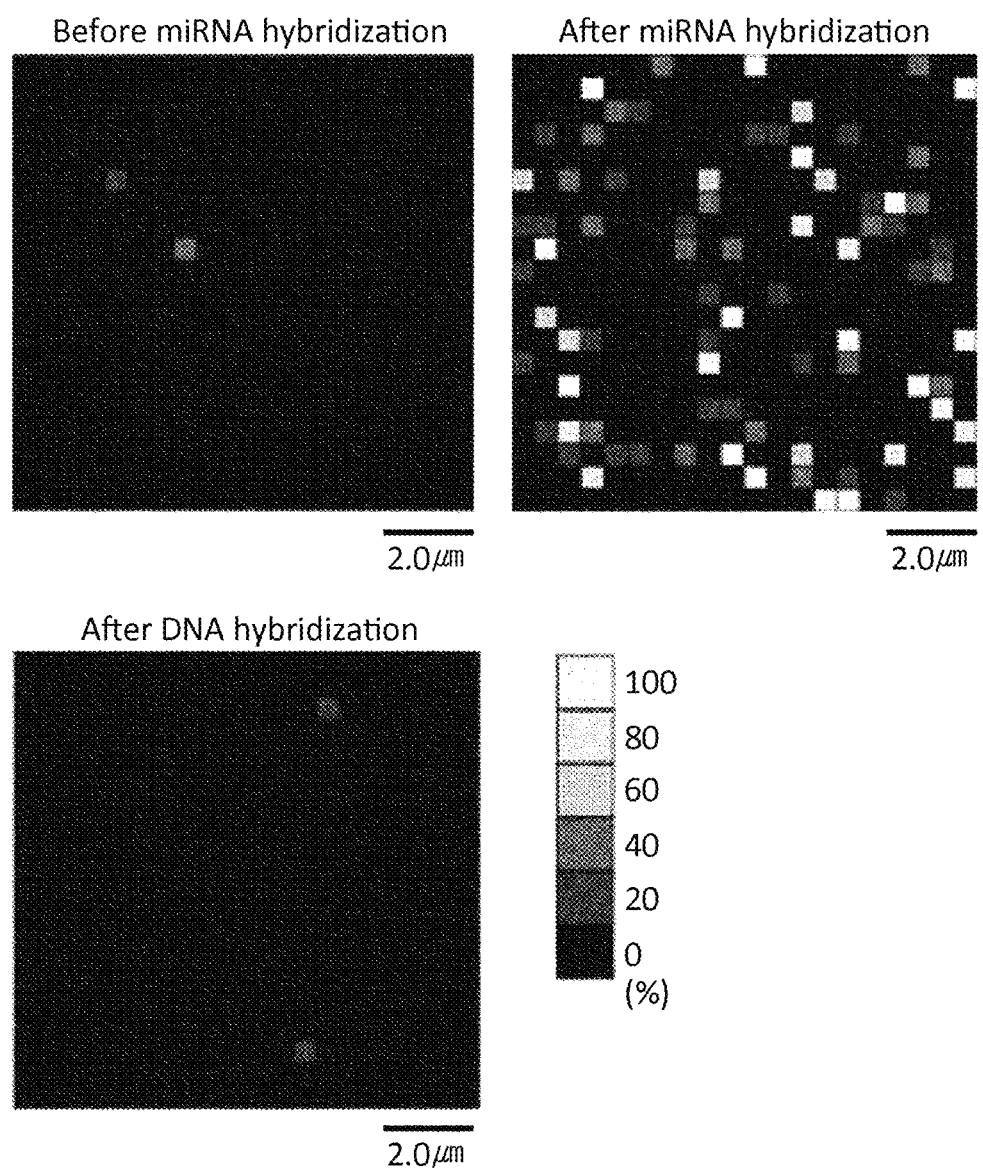
FIG. 5 is an example of adhesion force mapping illustrating a probability that adhesion force is observed. In this example, the force mapping was performed on an area of 10.0 μm×10.0 μm with a pixel size of 500 nanometers, and 5 times of measurement per pixel.

As can be seen in FIG. 5, when adhesion force-mapping was conducted at the probe DNA spot before hybridization with the miRNA or after hybridization with the miR-134 homologous DNA (10.0 μM), the probability of observing the specific force-distance curve was very low. In contrast, when the probe DNA was hybridized with miRNA (10.0 μM), the probability of observing adhesion force-distance curve is very high. Thus, the probe DNA-DNA (miR-134 homologous DNA) hybrid complex did not bind to the probe (i.e., HBD) in any significant manner.

Example 6: MiR-134 Analysis in Single Cell

MiRs-134 in a single cell were analyzed by targeting a neuron. Hippocampal neurons of a mouse (C57BL/6)

(DIV7) were cultured for 7 days. In one culture group, a KCl solution was injected into a culture solution so that the final solution concentration was 40 mM. The resulting neurons were stimulated for additional 2 hrs. In a control group, an aqueous solution without KCl was injected. It is known that under the above stimulation condition (KCl 40 mM, 2 hrs), miR-134s in the neurons increase 2 to 4 times. For verification at a single cell level, a single neuron was separated using a laser capture microdissection (LCM) method and the total RNA was extracted using a commercially available RNA extraction kit.

Figure 8:
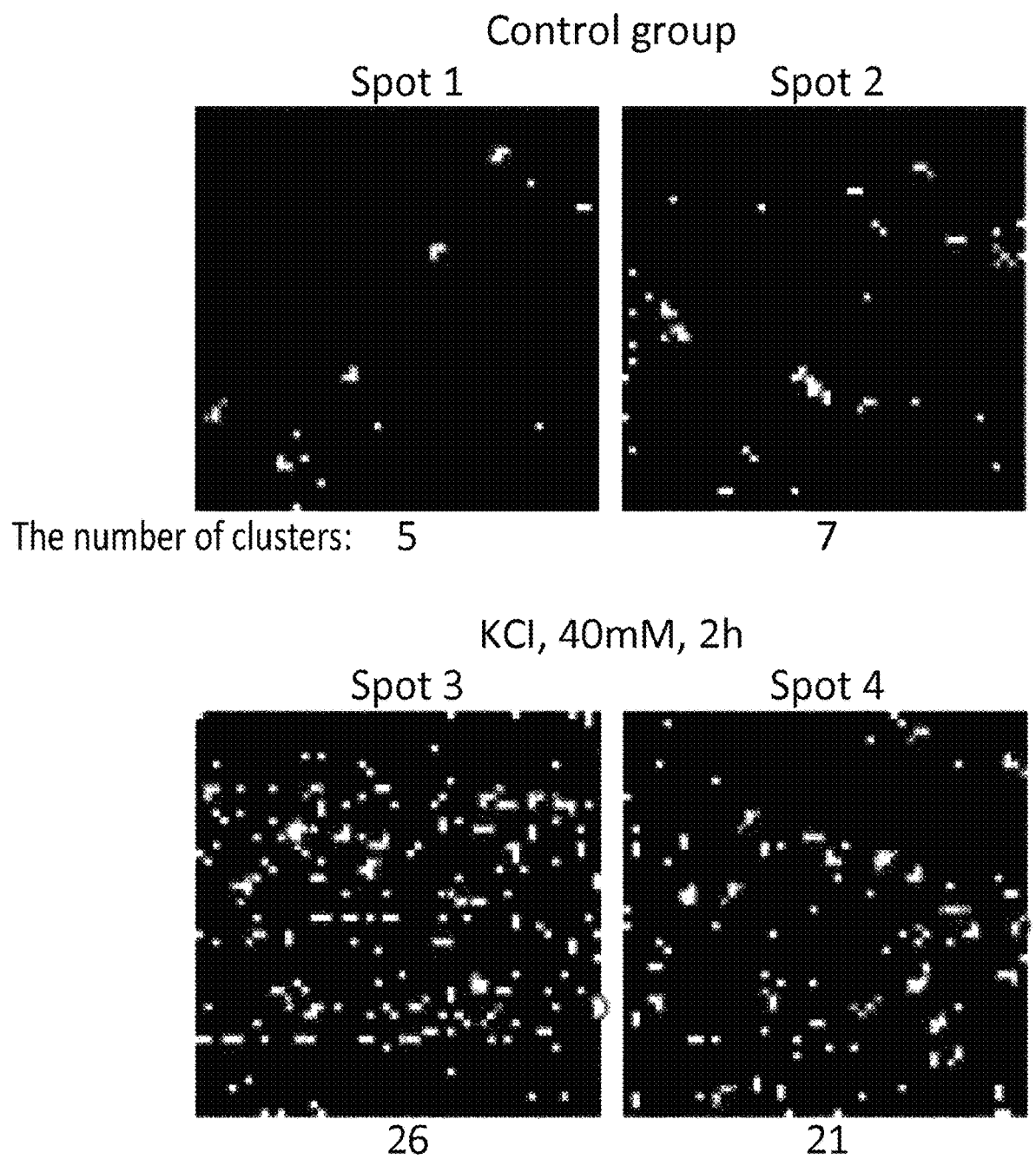
FIG. 8 is an example of analyzing target miRNAs in a single cell. An aqueous solution containing an RNA sample obtained from a single neuron is divided into two and two are analyzed on different spots, respectively. Cells stimulated with KCl and cells which are not stimulated with KCl are analyzed and compared (measured by 500 nm×500 nm, a pixel size of 10 nm, and 5 times per pixel). The yellow pixels are pixels where the adhesion force is observed.

An aqueous solution containing the extracted RNA was divided into two portions, and the two portions were hybridized on different probe DNA spots. Thereafter, the number of miR-134s captured on the substrate surface was calculated by adhesion force-mapping at each spot (500 nm×500 nm in size, with a pixel size of 10 nm, and scanning 5 times per pixel). The number of miR-134s present in the single neuron was determined by adding the numbers of miR-134 calculated at two spots. Cells stimulated with KCl and cells which were not stimulated with KCl were analyzed and compared. The results are shown in FIG. 8. The bright (i.e., "lighted") pixels are areas where the binding force was observed. The total number of double helixes (i.e., the probe DNA-target miRNA hybrid complex) was calculated using the following Equation:

The total number of double helixes in sample=(the number of double helixes per unit area of spot× (spot area/unit area))/(capture efficiency of miRNA on the probe spot %/100)

In a control group (no KCl in the aqueous solution), as shown in FIG. 8 about 1,100 miR-134s were present in the single neuronal cell. In contrast, about 4,600 miRs-134 were present in the stimulated cells (KCl in the aqueous solution). It should be noted that the difference in the result derived from each spot (two different portions of the same group) was significantly smaller than the difference between the cells (i.e., between the stimulated group and the control group). As can be seen, the miRNAs present in the single cell can be readily detected and/or quantified using the apparatus and the methods disclosed herein. The difference between the control group and the experimental group can also be determined at a single cell level.

Example 7. Purification of GST-Fused HBD

GST-fused HBD was cloned into the pGEX-4T-1 construct and expressed in BL21 (DE3) cells. The cells were cultured in LB medium containing carbenicillin, and protein expression was induced by the addition of 0.20 mM IPTG at 37 ÅãC for 4 h. The cultured cells were re-suspended in lysis buffer (50 mM Tris-HCl, 200 mM NaCl, 0.5% Tween 20 (v/v), 1.0 mM DTT, 2.0 mM EDTA, pH 8.0) containing a protease inhibitor cocktail (Roche) and were lysed by sonication. The lysate was centrifuged at 25,000 g at 4 ÅãC for 25 min, and the supernatant was loaded onto a GSH-agarose resin. GST-HBD protein was eluted with 50 mM Tris buffer containing 1.0 mM EDTA and 15 mM reduced glutathione (pH 9.5). The eluted proteins were concentrated in storage buffer (50 mM Tris-HCl, 200 mM NaCl, 2 mM EDTA, pH 8.0) using a centrifugal filter (10 kD cut off, EMD Millipore) and confirmed by SDS-PAGE.

Neuron Culture:

C57BL/6 mouse hippocampal neurons were dissected from postnatal day 1 pups and cultured on poly-L-lysine (Sigma)-coated plates and cover slips. Neurons were plated in neurobasal medium (Invitrogen) supplemented with 2.0% B27 (Invitrogen), 1.0% GlutaMAX™ (Invitrogen), 2.0% fetal bovine serum (Hyclone) and 1.0% penicillin/streptomycin (Invitrogen) (v/v) in a humidified 5% $CO_2$/95% $O_2$ incubator at 37° C. After 6-8 h, the medium was replaced with serum-free conditioned neurobasal medium. At DIV7, a group of neurons was treated with KCl (final concentration 40 mM) for 2 h before cell lysis, aspiration or fixation.

N2a Culture:

N2a cells were cultured on poly-L-lysine-coated cover slips. Cells were grown in 44.5% DMEM (Welgene) and 44.5% Opti-MEM (GIBCO) supplemented with 10% fetal bovine serum (Hyclone) and 1.0% penicillin/streptomycin (Invitrogen) (v/v) in a humidified 5% $CO_2$/95% $O_2$ incubator at 37° C.

Single-Cell Aspiration:

After KCl treatment, hippocampal neurons were moved into a whole-cell patch clamp setup. Neurons were continuously perfused with extracellular solution (119 mM NaCl, 2.5 mM KCl, 2.0 mM $MgSO_4$, 1.25 mM $NaH_2PO_4$, 26 mM $NaHCO_3$, 2.5 mM $CaCl_2$, and 10 mM dextrose, pH 7.4) at room temperature, and a whole-cell patch clamp was generated using borosilicate micropipettes (3-5 MΩ) filled with 3-5 μL internal solution (135 mM KCl, 10 mM NaCl, 2 mM $MgCl_2$, 0.5 mM EGTA, and 10 mM HEPES, pH 7.2 adjusted with KOH). SUPERase-In (2.0 μL $mL^{-1}$, Ambion) was also included in the internal solution to inhibit RNase activity. After a whole-cell patch clamp recording was obtained with a Multiclamp 700B amplifier (Molecular Devices), the cell was aspirated by applying negative pressure with a connected 50-ml glass syringe. The aspiration step took no longer than 5 min, and the recording electrode was cleaned after each aspiration to prevent cell-to-cell contamination. Cells exhibiting a >100 pA change in holding current during the aspiration were discarded.1 The aspirated cytoplasm was immediately delivered into an RNase-free PCR tube containing 7.0 μl QIAzol lysis solution by breaking the tip and applying positive pressure. To minimize the effect of RNases, all glassware, including micropipettes, were incubated at 170° C. overnight, and other equipment was cleaned with RNaseZap (Ambion).

Total RNA Extraction:

To isolate RNA from neurons in the culture plate, neurons were rinsed with ice-cold Dulbecco's PBS, and 500 μl QIAzol lysis solution was added. Cell lysis and total RNA extraction were performed for samples collected from the culture plate or single-cell aspiration using a miRNeasy Micro Kit (Qiagen) according to the manufacturer's protocol. The concentration (w/v) and purity of RNA extracted from neurons in a culture plate were determined by measuring the absorbance at 230, 260 and 280 nm with an ND-1000 spectrophotometer (NanoDrop Technologies).

Quantitative RT-PCR:

Total RNA samples and synthetic miR-134 were polyadenylated and reverse transcribed at 37° C. for 1 h using a miScript II RT Kit (Qiagen). cDNA made from the total RNA samples was diluted 20-fold for the PCR reactions. qPCR analysis was performed in triplicate on a LightCycler 2.0 (Roche) using a miScript SYBR Green PCR Kit and miR-134-specific primers (Qiagen), and the data were analyzed using an automatic cycle threshold setting. A standard curve was generated at each reaction from the cDNA of synthetic miR-134 prepared at five different concentrations (1.2 Å~108-1.2 Å~104 copies in the PCR reaction solution). The copy number of miR-134 in a single neuron was calculated assuming a total RNA mass of 20 pg per cell.

RNase H Treatment:

The probe spots or fixed cells were immersed in the RNase H reaction buffer (50 mM Tris-HCl, 75 mM KCl, 3 mM MgCl2, 10 mM DTT, pH 8.3) containing 20 units of RNase H (M0297, New England Biolabs) at room temperature for 2 h. The samples were rinsed with PBS and examined with AFM.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. An atomic force microscope comprising a cantilever, wherein said cantilever comprises a probing tip and a probe that is immobilized on said probing tip, wherein said probe comprises a hybrid binding domain (HBD) or a variant thereof, wherein said variant of HBD is elected from the group consisting of:
   an HBD linked to a glutathione S-transferase (GST);
   an HDB linked to a histidine-tag; and
   a biotinylated HBD,
and wherein said HBD is capable of binding to a minor groove of a DNA/RNA hybrid duplex.

2. The atomic force microscope of claim 1, wherein said HBD comprises an amino terminal (N-terminal) domain of a human ribonuclease 1 (RNase I).

3. The atomic force microscope of claim 1, wherein said HBD comprises an amino acid sequence of SEQ ID NO: 1.

4. The atomic force microscope of claim 1, wherein said probe comprises the variant of the HBD.

5. The atomic force microscope of claim 4, wherein in said variant of the HBD is said HBD linked to said GST, wherein said GST is immobilized on said probing tip and is attached to the N-terminal of said HBD.

---

SEQUENCE LISTING

```
<160> NUMBER OF SEQ ID NOS: 3

<210> SEQ ID NO 1
<211> LENGTH: 50
<212> TYPE: PRT
<213> ORGANISM: Artificial Sequence
<220> FEATURE:
<223> OTHER INFORMATION: HBD Protein

<400> SEQUENCE: 1

Met Phe Tyr Ala Val Arg Arg Gly Arg Lys Thr Gly Val Phe Leu Thr
1               5                   10                  15

Trp Asn Glu Cys Arg Ala Gln Val Asp Arg Phe Pro Ala Ala Arg Phe
            20                  25                  30

Lys Lys Phe Ala Thr Glu Asp Glu Ala Trp Ala Phe Val Arg Lys Ser
        35                  40                  45

Ala Ser
    50

<210> SEQ ID NO 2
<211> LENGTH: 22
<212> TYPE: RNA
<213> ORGANISM: Artificial Sequence
<220> FEATURE:
<223> OTHER INFORMATION: miR-134

<400> SEQUENCE: 2
ugugacuggu ugaccagagg gg                                              22

<210> SEQ ID NO 3
<211> LENGTH: 22
<212> TYPE: DNA
<213> ORGANISM: Artificial Sequence
<220> FEATURE:
<223> OTHER INFORMATION: Probe DNA

<400> SEQUENCE: 3
cccctctggt caaccagtca ca                                              22
```

6. The atomic force microscope of claim 1, wherein said probe is capable of complementarily binding to a target microRNA (miRNA).

7. The atomic force microscope of claim 1, wherein said probe is capable of binding to a 2'—OH group of two consecutive bases of an RNA strand; three phosphodeoxyribose units of a DNA strand, or a combination thereof.

8. A method for detecting the presence of a target microRNA in a sample without labeling or amplifying, said method comprising:
  (a) contacting a substrate comprising a probe DNA that is immobilized on the surface of said substrate with a sample under conditions sufficient to form a DNA/RNA hybrid complex when a target microRNA (miRNA) is present in the sample and
  (b) detecting a presence of said DNA/RNA hybrid complex using the atomic force microscope of claim 1.

9. The method of claim 8, wherein said probe DNA comprises a nucleotide sequence that is complementary to said target miRNA.

10. The method of claim 8 further comprising the step of determining the amount of said target miRNA in said sample.

11. The method of claim 10, wherein said step of determining the amount of said target miRNA in said sample comprises:
  determining the number of said DNA/RNA hybrid complexes detected per spot area of said substrate and
  calculating a total number of said target miRNA in said sample using Equation 1:

$$T_{miRNA} = (N \times (S/U))/(E/100) \quad \text{(Eq. 1)},$$

wherein
$T_{miRNA}$ = total number of said target miRNA;
N = the number of said target miRNA per unit area of spot;
S = total spot area within said substrate;
U = unit area of spot; and
E = % capture efficiency of miRNA by said probe.

12. The method of claim 8, wherein said step of detecting the presence of said DNA/RNA hybrid complex comprises (i) determining a site where the adhesion force is observed at four consecutive pixels of 8 nm pixel size or (ii) determining three consecutive pixels where an adhesion force is observed at three consecutive pixels of 10 nm pixel size.

13. The method of claim 8, wherein the sample is a fluid sample, and wherein the concentration of the target miRNA in the sample is $5 \times 10^{-20}$ to $2 \times 10^{-13}$ M.

14. The method of claim 8, wherein a size of a probe DNA spot is calculated by an equation selected from the group consisting of:

$$S_D(\mu m) = ([M] \times 10^{19}/5)^{0.5} \quad \text{(Eq. 2) and}$$

$$S_D(\mu m) = ([unit]/10)^{0.5} \quad \text{(Eq. 3)},$$

wherein
$S_D$ is Probe DNA spot diameter;
[M] is miRNA concentration; and
[unit] is miRNA number.

15. The method of claim 8, wherein the substrate is selected from the group consisting of glass, metal, plastic, silicon, silicate, ceramic, a semiconductor, synthetic organic metal, a synthetic semiconductor, an alloy, and a combination thereof.

16. The method of claim 8, wherein a site of the HBD binding to the DNA/RNA hybrid complex comprises:
  Y3, K33, and K34 of the HBD bound with the DNA strand of the DNA/RNA hybrid complex;
  W17 and F32 of the HBD bound with the RNA strand of the DNA/RNA hybrid complex; and
  a combination thereof.

17. The method of claim 8, wherein said sample is obtained from a single cell.

* * * * *